United States Patent [19]
Kain et al.

[11] Patent Number: 5,847,400
[45] Date of Patent: Dec. 8, 1998

[54] FLUORESCENCE IMAGING SYSTEM HAVING REDUCED BACKGROUND FLUORESCENCE

[75] Inventors: Robert C. Kain, San Jose, Calif.; Christopher C. Alexay, Walpole, N.H.

[73] Assignee: Molecular Dynamics, Inc., Sunnyvale, Calif.

[21] Appl. No.: 791,684

[22] Filed: Jan. 30, 1997

Related U.S. Application Data

[63] Continuation-in-part of Ser. No. 595,355, Feb. 1, 1996, Pat. No. 5,646,411.

[51] Int. Cl.[6] .................................................. G01N 21/64
[52] U.S. Cl. ................................. 250/458.1; 250/461.1; 250/461.2
[58] Field of Search ............................. 250/461.2, 461.1, 250/458.1; 356/445

[56] References Cited

U.S. PATENT DOCUMENTS

| | | |
|---|---|---|
| 4,006,360 | 2/1977 | Mueller . |
| 4,284,897 | 8/1981 | Sawamura et al. . |
| 4,877,965 | 10/1989 | Dandliker et al. . |
| 5,022,757 | 6/1991 | Modell . |
| 5,091,652 | 2/1992 | Mathies et al. . |
| 5,091,653 | 2/1992 | Creager et al. . |
| 5,095,213 | 3/1992 | Strongin . |
| 5,192,980 | 3/1993 | Dixon et al. . |
| 5,260,578 | 11/1993 | Bliton et al. . |
| 5,296,700 | 3/1994 | Kumagai . |
| 5,381,224 | 1/1995 | Dixon et al. . |
| 5,404,247 | 4/1995 | Cobb et al. . |
| 5,504,336 | 4/1996 | Noguchi . |
| 5,646,411 | 7/1997 | Kain et al. ............................ 250/458.1 |
| 5,713,364 | 2/1998 | DeBaryshe et al. ..................... 128/664 |

OTHER PUBLICATIONS

Shoemaker et al., "An Ultrafast Laser Scanner Microscope for Digital Image Analysis", *IEEE Transactions on Biomedical Engineering*, vol. BME–29, No. 2, pp. 82–91 (Feb. 1982).

*Primary Examiner*—Constantine Hannaher
*Attorney, Agent, or Firm*—Thomas Schneck; John P. McGuire, Jr.

[57] ABSTRACT

A coaxial illumination and collection laser scanning system designed to provide increased sensitivity by reducing autofluorescence while having a substantially uniform detection sensitivity across the field of view of an objective lens by reducing lateral chromatic aberrations at the expense of amplifying axial chromatic aberrations. Axial chromatic aberrations in the system are removed in the path of a retro-beam. A laser is in optical communication with the objective lens. The laser produces a collimated beam of coherent light that is directed by a scanner through the objective lens to illuminate a raster of spots on the sample's surface, thereby stimulating a series of small regions of the sample to emit light. The system may be used as a confocal or non-confocal imaging system.

16 Claims, 9 Drawing Sheets

FLUORESCENCE IMAGING SYSTEM HAVING REDUCED BACKGROUND FLUORESCENCE

CROSS-REFERENCE TO RELATED APPLICATION

This is a continuation-in-part of patent application Ser. No. 08/595,355 filed on Feb. 1, 1996, which issued as U.S. Pat. No. 5,646,411 on Jul. 8, 1997.

TECHNICAL FIELD

The present invention relates to laser scanning imaging systems, particularly for use in fluorescence imaging.

BACKGROUND ART

Fluorescence microscopy is often used in the fields of molecular biology, biochemistry and other life sciences. One such use is in identifying a specific antigen using antibodies. Antibodies are proteins produced by vertebrates as a defense against infection. They are made of millions of different forms, each having a different binding site and specifically recognizing the antigen that induces its production. To identify an antigen, a sample of cells is provided that contains specific antibodies coupled to a fluorescent dye. The cells are then assessed for their fluorescence. Taking advantage of the precise antigen specificity of antibodies, the cells having fluorescent properties are known to contain a specific antigen.

Originally, the fluorescence of cells was assessed manually by visual inspection, using conventional microscopy. This proved time-consuming and costly. The need for high-speed automated systems became manifest. Many high-speed imaging systems, such as confocal microscopes, are available for assaying cell samples. The illumination and collection optics, along with their relative geometry, determine in large part the parameters of the other system elements.

To increase the sensitivity of the fluorescent microscopy systems, a number of steps have been taken, including improved optical elements that demonstrate reduced chromatic aberrations. Additionally, steps have been taken to improve the signal-to-noise ratio by using techniques that increase the saliency of fluorescence emitted by a sample among background fluorescence, fluorescence not emitted by the sample. Similar to chromatic aberrations, a substantial amount of the background fluorescence in a system arises from the optical components that make upon the same.

There are many optical components available. For example, U.S. Pat. No. 5,404,247 to Cobb et al. discloses an air-spaced, diffraction limited, seven element telecentric f-θ lens. However, the design of a classical f-θ lens is primarily for monochromatic illumination which can often times exacerbate chromatic aberrations of a fluorescent microscopy system.

A prior art high-speed imaging system is shown in FIG. 1 and includes an f-θ objective 10 positioned above a sample 11 so that the surfaces of the objective are perpendicular to the sample's normal. A laser light source 12 produces a beam 13. The objective 10 directs the beam 13 to illuminate a spot on the sample's surface. An oscillating reflective surface 14 is disposed at the pupil 15 of the system, between the light source 12 and the objective 10, to deflect the beam 13 back and forth along one axis. The sample is placed on a table to move the sample in a direction perpendicular to the first scan direction, thereby resulting in a two dimensional scan pattern on the sample's surface. The objective is not designed for coaxial collection resulting in light reflected from the sample surface being collected by a condenser assembly 16 that is separate and apart from the objective. Such a geometry results in increased system footprint, increased optical complexity and a limitation of solid angle collection. The collected light is then imaged on a photo-detector 17.

A prior art high-speed imaging system, similar to that described with respect to FIG. 1, is disclosed by Richard L. Shoemaker et al., in "An Ultrafast Laser Scanner Microscope for Digital Imaging Analysis", *IEEE Transactions on Biomedical Engineering*, Vol. BME-29, No. 2, Feb. 1982, pp. 82–91. The principal difference between these two systems concerns the scanning device. Instead of a galvanometric scanner, Shoemaker et al. require the use of a rotating polygon mirror to scan the spot over the sample's surface.

Another prior art high-speed imaging system is disclosed in U.S. Pat. No. 4,284,897 by Sawamura et al., in which laser light is reflected through two galvanometric mirrors and one dichroic mirror to direct a beam through an objective and illuminate a spot on a sample's surface. The galvanometric mirrors are swung in appropriate directions to allow the spot to scan over the entire surface of the sample. In response to the illuminating spot, the sample emits fluorescence light. The objective, serving as a condenser lens, transmits the light back through a first dichroic mirror. Positioned behind the first dichroic mirror is a second dichroic mirror that splits the fluorescent light into a light produced by a first probe at a first wavelength and light produced by a second probe at a second wavelength. The first and second wavelengths are transmitted to respective photo-detectors.

U.S. Pat. No. 5,296,700 to Kumagai discloses a fluorescent confocal microscope which includes, in pertinent part, an intermediary optical system disposed between a pair of scan mirrors and an objective optical system. The intermediary optical system is designed to cancel chromatic aberrations of magnification introduced by the objective optical system.

U.S. Pat. No. 5,260,578 to Bliton et al. discloses a scanning confocal microscope which includes, in pertinent part, two beam sources. One beam source produces ultra violet light. One beam source produces visible light. An optical assembly is included in the common optical train to correct chromatically induced scanning errors.

U.S. Pat. No. 5,381,224 by Dixon et al. discloses a scanning laser imaging system which allows simultaneous confocal and non-confocal imaging of reflected light. The system includes, in pertinent part, a laser producing a beam which traverses a beam expander and impinges upon a single mirror disposed in an optical axis, which is defined by an objective lens. The objective lens directs the beam onto a sample, which is disposed upon a moveable stage. Disposed between the objective and the sample is a beam splitter designed to collect light emitted from the sample. The beam splitter directs a portion of light emitted from the sample onto a condenser lens, which in turn directs it onto a non-confocal detector. A portion of the light collected by the beam splitter is directed along the same path as the beam, but in an opposite direction, forming a retro-beam. The retro-beam impinges upon a second beam splitter, positioned between the scan mirror and the laser. The second beam splitter directs the light onto a focusing lens. The focusing lens is positioned proximate to a confocal field stop, having an aperture.

In U.S. Pat. No. 5,095,213 to Strongin, a novel microscope slide is employed to reduce background fluorescence. The slide is made of a plastic that has optical properties rendering it opaque and substantially non-fluorescent. These optical properties are achieved by providing the plastic with a sufficient quantity of black carbon powder.

U.S. Pat. No. 5,091,653 to Creager et al. discloses an apparatus and method for reducing background fluorescence. The apparatus is a fiber optic dosimeter. The method of reducing background fluorescence includes modulating an infra-red stimulating source. This allows for measurement of background fluorescence during radiation exposure when infra-red stimulating radiation is not applied. The background fluorescence is then subtracted from the gross signal under infra-red stimulation.

U.S. Pat. No. 4,877,965 to Dandliker et al. discloses a fluorometer for measuring a particular fluorescence emanating from a specimen. The stimulating radiation is generated in bursts which are then directed toward the specimen to produce a fluorescence. The timing of the detection of the fluorescence is controlled to take advantage of differences in optical decay between background fluorescence and fluorescence emitted from the specimen. To that end, the stimulating radiation is directed onto the specimen in bursts, and the light path to the detector is periodically blocked.

Although the prior art systems are suitable for fluorescent microscopy, they require additional optics to correct optical aberrations over a scan field and to efficiently collect light emitted from a sample. They also necessitate specialized components to reduce background fluorescence. This results in a net increase in the system's cost and size.

What is needed, therefore, is to provide a high-speed, low cost, laser scanning system with improved signal-to-noise ratio that will provide point by point image of a sample on both a micro and macro scale.

A further need exists to provide an imaging system of a substantially smaller size than the prior art systems that affords a larger scan field than existing coaxial illumination and collection systems.

SUMMARY OF THE INVENTION

Provided is a coaxial illumination and collection laser scanning system designed to provide increased sensitivity by reducing auto-fluorescence while having a substantially uniform detection sensitivity across a planar field of view by reducing chromatic aberrations. For purposes of this application, auto-fluorescence is defined as fluorescent radiation not associated with fluorescent radiation of the sample region under test. Specifically, the objective lens is formed so as to avoid the application of excess auto-fluorescing materials, such as adhesive, in the optical path of the lens. Also, the objective lens is designed to reduce lateral chromatic aberrations at the expense of increasing axial chromatic aberrations. The axial chromatic aberrations are removed from the system using another lens already existing in the system.

Auto-fluorescence from the remaining optical components of the system is removed by selective placement of filters along the optical path. Specifically, it was found that auto-fluorescence associated with these optical components is seen by a detector of the system as arriving over two different trajectories. One of the trajectories is associated with the through-focus-curve of the objective lens. That is, auto-fluorescence occurring proximate to the sample plane is directed onto a detector via the objective lens directing the same thereon. Auto-fluorescence occurring distal from the sample plane follows a scattering trajectory. This auto-fluorescence radiates spherically as though emanating from a point source.

A laser is in optical communication with the objective lens. The laser produces a collimated beam of coherent light that is directed through the objective lens to illuminate a spot on a sample, thereby stimulating a small region of the sample to emit light. The objective lens also serves as a condenser and collects the light emitted by the sample. The objective lens is designed with correction for lateral chromatic aberrations and without correction for axial chromatic aberrations. The objective lens directs the collected light back along the identical path traveled by the incident beam, but in an opposite direction. A wavelength discriminating dichroic filter is placed along the optical axis between the laser and the objective lens to separate the emitted light from the incident beam, and a focusing lens directs the collected light onto a photo-detector. The photo-detector produces a signal in response to the emitted light sensed, representing the sample emitting the light. The focusing lens is a doublet lens that uses two elements in order to keep a constant focal length with different wavelengths of light. The doublet lens is disposed in the path of a retro-beam and is optically designed to introduce axial chromatic aberrations necessary to correct for axial chromatic aberrations introduced elsewhere in the system, e.g., by the objective lens. To scan over the entire sample, a two dimensional scanning device having a reflecting element is disposed in the path of the incident beam. A display device is provided and synchronized with the scanning device to reproduce an image of the sample.

In another embodiment, a plurality of lasers are provided, each of which emits one or more wavelengths different from the remaining lasers. Each of the plurality of lasers are in optical communication with a common beam expander providing the incident beam with a plurality of wavelengths of light. The common beam expander has optical properties that introduce axial chromatic aberrations to cancel axial chromatic aberrations introduced by the objective lens, with respect to the incident beam.

BEST MODE FOR CARRYING OUT THE INVENTION

Figure 2:
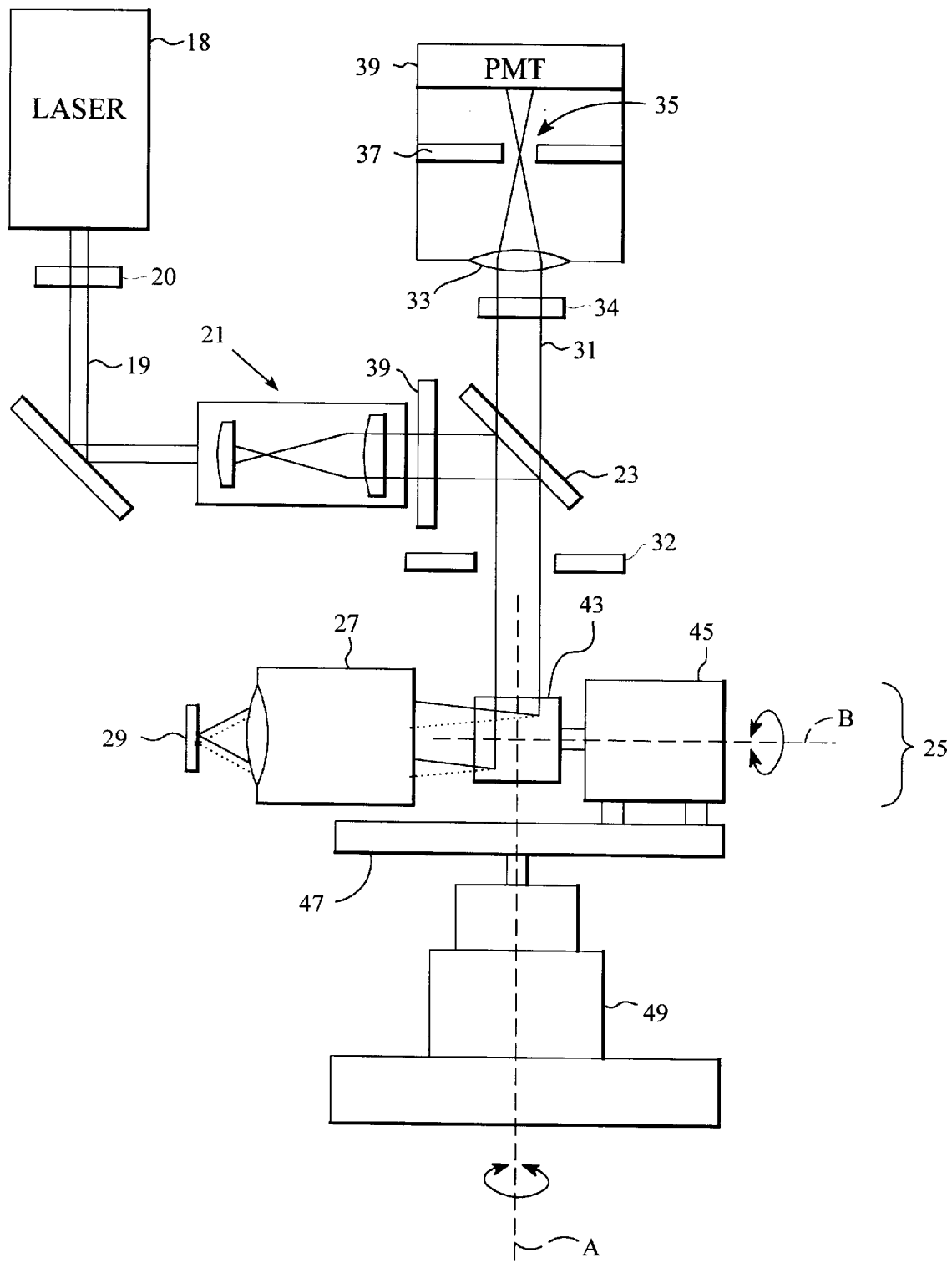
FIG. 2 is a side view of optical components of the present invention.

FIG. 2 shows a light source 18 producing an excitation/incident beam 19 of light. Beam 19 is directed through an excitation filter 20 to reduce unwanted wavelengths in the incident beam 19. Upon exiting the excitation filter 20, beam 19 impinges upon a beam expander 21 and then a beam splitter 23. Beam splitter 23 directs beam 19 onto a two dimensional scanning device 25. Two dimensional scanning device 25 directs beam 19 through an objective lens 27. Objective lens 27 directs beam 19 to illuminate a spot (not shown) on a sample 29, thereby stimulating a small region of sample 29 to emit light. Typically, the light emitted by sample 29 is fluorescent. Objective lens 27, acting as a condenser, collects the fluorescent light, forms a retro-beam 31 and directs retro-beam 31 along an identical path of incident beam 19, but in an opposite direction. Retro-beam 31 passes through a pupil stop 32, consisting of a spatial filter with an aperture. After exiting pupil stop 32, retro-beam 31 impinges upon beam splitter 23. Beam splitter 23 separates fluorescent light from the laser light and directs retro-beam 31 onto a focusing lens 33 via band pass filter 34. Focusing lens 33 directs retrobeam 31 onto a transmissive aperture 35 of a spatial filter 37, thereby causing retro-beam 31 to impinge upon a photodetector 39.

It is preferred that light source 18 is a laser producing a collimated beam of coherent light. It is possible, however, to use a non-coherent light source optically coupled to collimating optics to create an incident light beam, e.g., a light emitting diode. If a non-coherent light source, such as an LED, is employed, a pinhole and a collimating lens are disposed in front of the LED to create a collimated excitation/incident beam capable of being focused to a small spot. Band pass filter 34 typically rejects the excitation wavelengths while transmitting longer wavelengths.

Beam splitter 23 may be any known in the art, so long as it is capable of separating the light of the incident beam from the light of the retro-beam. For example, beam splitter 23 may be a dichroic filter or a 50% beam splitter. Alternatively, a polarization sensitive beam splitter may be used to achieve separation of beams 19 and 31. This embodiment could include a ¼ waveplate positioned between the beam splitter and the objective. This would cause beam 19 exiting the ¼ waveplate to be circularly polarized. Also, the separating means may be a fresnel reflector. Sample 29 is illuminated point by point, scanning the spot in a raster scan fashion over the entire area of sample 29.

Any scanning mechanism that provides a two dimensional scan may be used, e.g., a rotating polygonal mirror, rotating holographic scanner, or oscillating prisms. Also, an acousto-optic deflector or a penta-prism scanning deflector may be employed. The preferred embodiment, however, is to employ a scanning system having one beam reflecting element 43 in the path of the incident beam which is pivotable about two perpendicular axes. Reflecting element 43 is a planar mirror, but this is not essential. The mirror may be concave or convex. Refractive or diffractive deflecting elements may also be used as reflecting element 43. Mirror 43 is pivotable about axis A. Mirror 43 may be moved by any means known in the art, such as motor 45, but is typically a galvanometer mirror. Mirror 43 and motor 45 rest atop a moveable platform 47 that is rotated by a stepper motor 49. Stepper motor 49 moves platform 47 to pivot mirror 43 about axis B, which is orthogonal to axis A.

Figure 3:
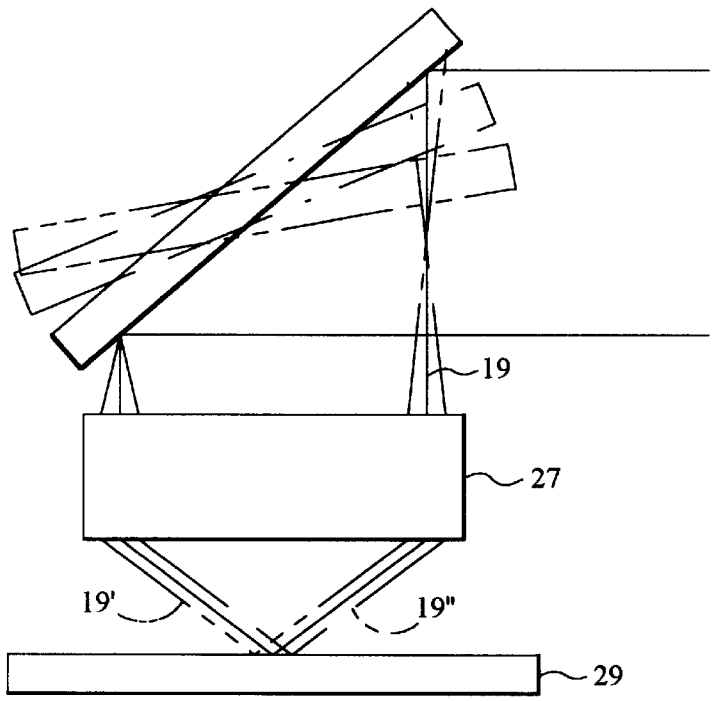
FIG. 3 is a detailed view of a scanning beam passing through the objective shown in FIG. 2.

Referring to FIG. 3, objective lens 27 typically forms an external pupil of the system and affords coaxial illumination and collection. To maximize collection efficiency, it is preferred that objective lens 27 have a large numerical aperture. With respect to incident beam 19, objective lens 27 is afocal in the image plane. Objective lens 27 is typically telecentric, or near telecentric. The telecentricity of objective lens 27 results in sample 29's surface always lying at a right angle with respect to the chief ray of incident beam 19, exiting objective lens 27. With respect to incident beam 19, the objective plane is proximate to sample 29. Beam 19 is shown entering objective lens 27 at three different positions, with beam 19 having a different angle of incidence at each position. Regardless of beam 19's angle of incidence on objective lens 27, the chief ray of beam 19 exiting objective lens 27 is orthogonal to sample 29's surface. One advantage of having this telecentric objective is that it renders the system magnification relatively insensitive to errors in focus position. In addition, objective lens 27 must be designed to operate over a broad band of wavelengths of light, e.g., the primary wavelength plus approximately 200 nm, or greater. This allows objective lens 27 to operate with lasers of various wavelengths and to collect light from a wide variety of fluorochromes.

Figure 4:
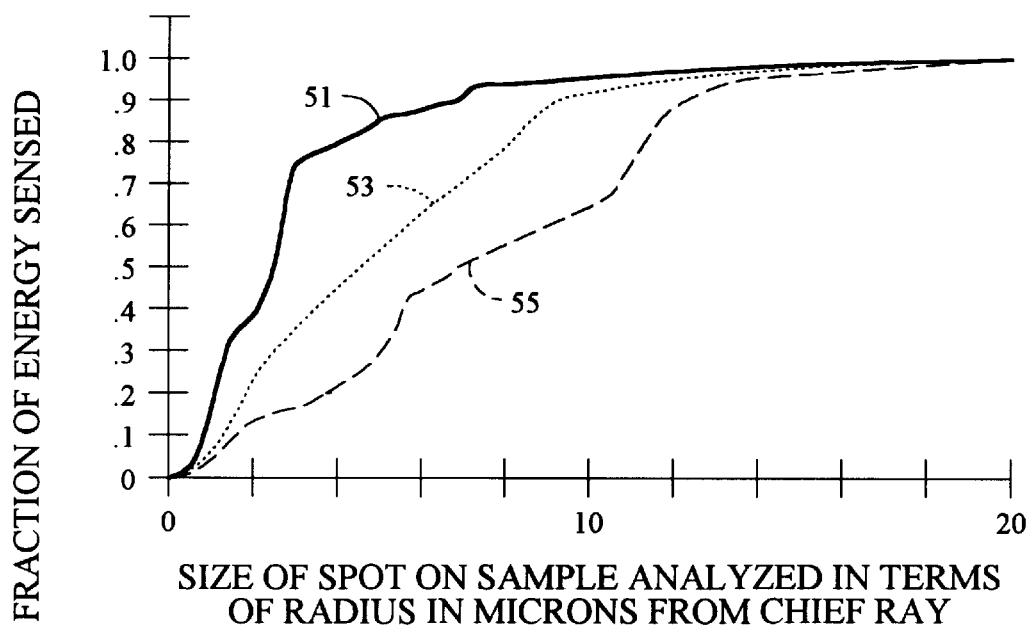
FIG. 4 is a graph showing an amount of optical energy impinging upon a detector disposed in an image plane using a common microscope system.
Figure 5:
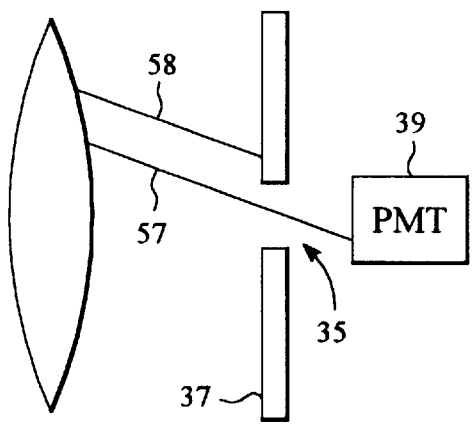
FIG. 5 is a schematic view showing the effects of lateral chromatic aberrations.

An important aspect of the system is to reduce an amount of optical loss in the field of view due to chromatic aberrations, which reduces the detection sensitivity of the system. FIG. 4 shows the relationship between field position and the relative detection sensitivity of a system not being corrected for lateral chromatic aberrations, as a function of the fraction of optical energy sensed versus size of the spot impinging upon sample 29. The amount of light detected on the optical axis 51, as defined by an objective lens, is substantially greater than the amount of light detected at a half field position 53. The lowest amount of light detected was at a full field 55 position, with the field of view defined by the objective lens. Lateral chromatic aberrations increase at larger field angles. The non-uniformity of light detected across the field of view of the lens in the system is typically a result of lateral chromatic aberrations and other field degradations such as coma. Referring to FIGS. 5 and 2, lateral chromatic aberrations may cause a reduction in detection sensitivity by allowing, e.g., green wavelengths 57 of light to pass through aperture 35 while causing longer yellow wavelengths 58 to be blocked by field stop 37.

To avoid the problems associated with lateral chromatic aberrations, it is preferred that objective lens 27 correct for all lateral chromatic aberrations in the scanning system. This may be accomplished by reducing the field of view of the objective. However, there are advantages in providing objective lens 27 with a large field of view. For example, a large (macro) field of view is useful for scanning large arrays of samples, e.g., planar field arrays containing up to a million specimens. Nonetheless, the increased field of view exacerbates the problems with lateral chromatic aberrations, because there is increasing difficulty in correcting lateral chromatic aberrations as the lens' field of view increases. The macro field of view makes lateral chromatic aberrations more pronounced, thereby making it more difficult to provide a uniform resolution across the field.

Considering the aforementioned concepts, the parameters for two implementations of objective lens 27 are as follows:

TABLE 1

|  | Micro Objective | Macro Objective |
| --- | --- | --- |
| Scan Area (diagonal) | 1 mm | 1 cm |
| Resolution | 0.6 μm | 10 μm |
| Numerical Aperture | 0.50 | 0.25 |
| Intensity Uniformity | 95% | 95% |
| Spatial Uniformity | 98% | 98% |
| Polychromatic Range | 500–750 nm | 500–750 nm |
| Thru focus sensitivity | 1% (signal change over 20 μm) | 1% (signal change over 100 μm) |
| Field Flatness Variation | +/−10 μm | +/−20 μm |
| Working Distance | 3 mm | 3.5 mm |
| Focal Length | 22 mm | 25 mm |
| Pupil Size | 25 mm | 13 mm |

As can be seen above, the micro and macro objectives described may allow the system to provide between 0.6 to 10 μm resolution.

Figure 6:
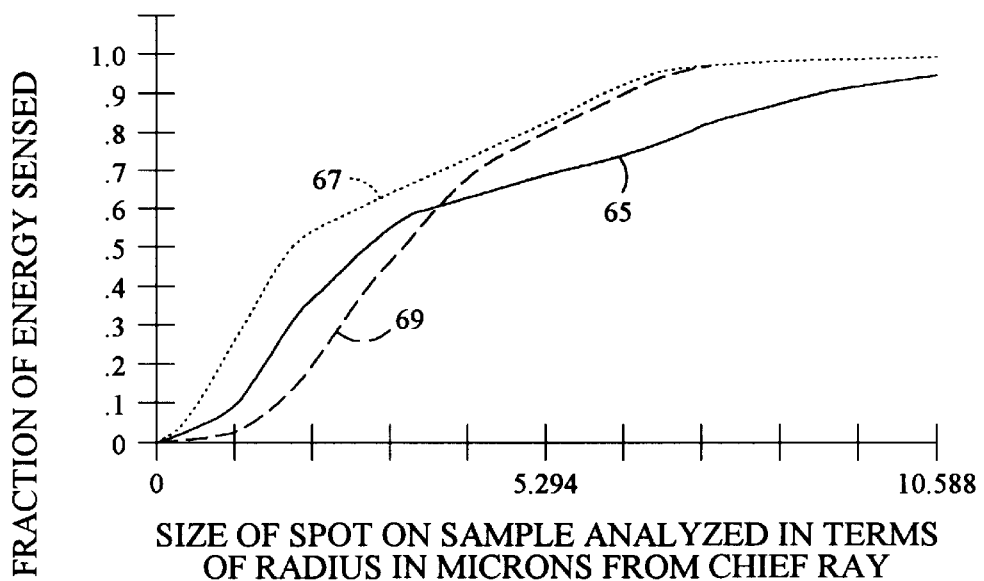
FIG. 6 is a graph showing an amount of optical energy impinging upon a detector in an image plane employing a large field objective lens of the present invention.
Figure 7:
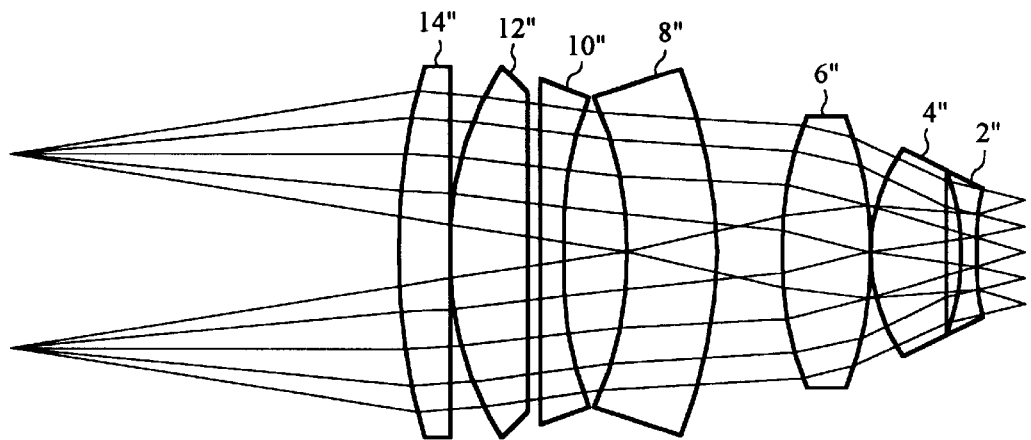
FIG. 7 is a schematic view of optical elements which comprise a large field objective lens of the present invention.

FIG. 6 shows a reduction in lateral chromatic aberrations of the macro objective lens which is achieved at the expense of amplifying axial chromatic aberrations. The increased axial chromatic aberrations are shown by the amount of light detected, at the 3 μm position, being substantially less than that shown in FIG. 4. Specifically, sensed by detector 39 is approximately 40% of the on axis light 65 impinging upon sample 29, 3 μm from the chief ray. In FIG. 4, the amount of on axis light 51 detected 3 μm from the chief ray was nearly 80%. Nonetheless, the overall effect of lateral chromatic aberrations is shown to be substantially reduced. This is demonstrated by the amount of light detected for any given spot size being substantially the same for light at the on axis 65, half field light 67 and full field 69 positions, i.e., there exists substantial uniformity of detection sensitivity across the field of view of the macro objective lens. Additionally, FIG. 6 shows that at 10 μm from the chief ray, collection from all field points is greater than 90%. FIG. 7 shows the optical elements of the macro objective lens, and the specifications are as follows:

TABLE 2

MACRO OBJECTIVE LENS

| Surface | Radius (mm) | Thickness (mm) | Material | Aperture (mm) |
| --- | --- | --- | --- | --- |
| STO |  | 27.67 |  |  |
| 2" | 29.95 | 3.89 | Schott_SK14 | 24 |
| 3 | 224.24 | 0.20 | air | 24 |
| 4" | 19.85 | 5.21 | SK14 | 24 |
| 5 | 136.67 | 0.65 | air | 20 |
| 6" | 134.23 | 2.10 | SF11 | 22 |
| 7 | 24.80 | 3.84 | air | 18 |
| 8" | −28.59 | 6.44 | SF5 | 18 |
| 9 | −60.20 | 4.86 | air | 22 |
| 10" | 27.86 | 5.73 | SK14 | 18.6 |
| 11 | −36.27 | 0.24 | air | 18.6 |
| 12" | 11.40 | 5.02 | SK14 | 14 |
| 13 | 88.81 | 0.69 | air | 11.6 |
| 14" | −33.76 | 1.32 | SF11 | 11.6 |
| 15 | 11.90 | 3.69 | air | 9 |

The aforementioned lens parameters and specifications are merely exemplary. The lens design may be adjusted to provide larger and smaller fields, as desired. This may be achieved by modifying lens radii, thickness, glass type, etc. Lenses with vastly different parameters may be designed to afford optimum performance at other resolutions and field sizes. Additionally, lenses could be designed for the same resolution and field size, as the aforementioned lenses, while satisfying different parameters, e.g., working distance and field flatness.

Figure 1:
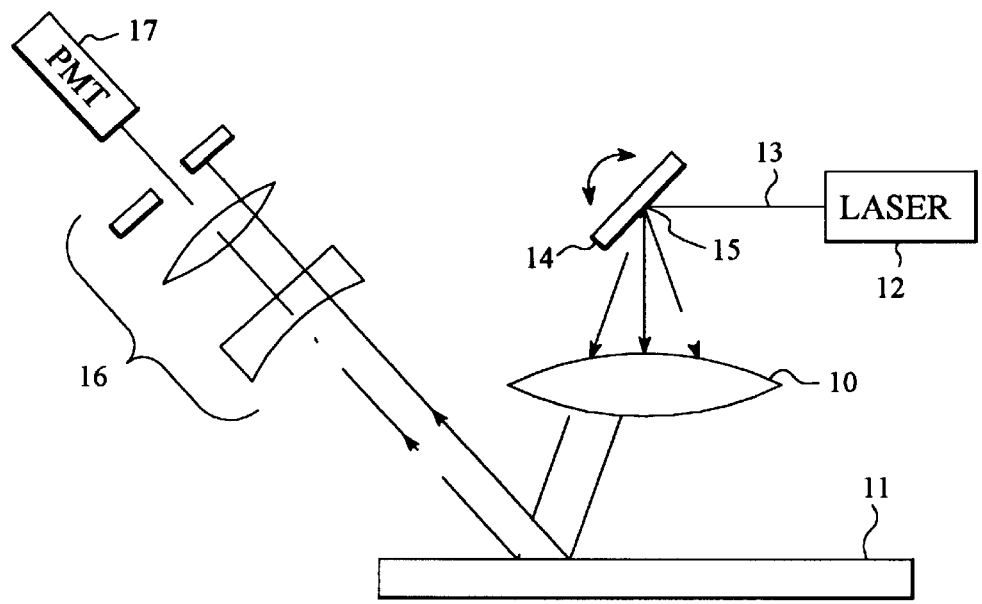
FIG. 1 is a simplified side view of a laser scanning microscope of the prior art.
Figure 8:
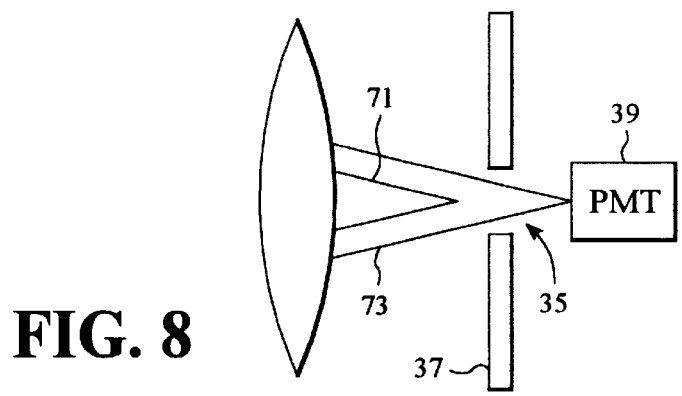
FIG. 8 is a plan view of optical components showing the effects of axial chromatic aberrations.

Referring to FIG. 8, similar to lateral chromatic aberrations, axial chromatic aberrations reduce the detection sensitivity of the system by having the focal length of a lens being wavelength dependent. For example, green wavelengths 71 of light focus before impinging upon detector 39, while the longer yellow wavelengths 73 of light are sensed by detector 39. Unlike lateral chromatic aberrations, however, axial chromatic aberrations do not change with the field position. Thus, the axial chromatic aberrations introduced by objective lens 27 may be kept constant, while correcting for lateral chromatic aberrations. Referring again to FIG. 1, because incident beam 19 is monochromatic, there is no need to correct axial aberrations in the incident path. Rather, axial chromatic aberrations may be corrected in the return (retro) path. It is preferred that focusing lens 33 corrects, or removes, all axial chromatic aberrations in the system. This allows manufacturing a less expensive objective lens 27, because correcting for both axial and lateral chromatic aberrations in a single lens greatly increases costs. In addition, the size/foot print of the system is kept to a minimum. As focusing lens 33 is necessary to condense retro-beam 31 onto aperture 35, no additional optics are included to reduce axial aberrations. Typically, focusing lens 33 is a doublet having the optical properties necessary to correct axial chromatic aberrations of the system. Focusing lens 33 could be composed of binary elements or any other design known in the art which focuses a beam and corrects axial chromatic aberrations.

Referring again to FIG. 2, an advantage with the objective lens design described above in Table 2 is that the auto-fluorescence of the system is greatly reduced. Specifically, it was found that auto-fluorescence associated with the optical components in the system is seen by detector 39 as arriving over two different trajectories. Auto-fluorescence emanating proximate to sample 29 generally follows the path of retro-beam. This holds true for auto-fluorescence that emanates from the optical elements of objective 27, or any other auto-fluorescence that falls within the through-focus-curve of objective 27. As such, this auto-fluorescence is referred to as through-focus auto-fluorescence (TFA). Auto-fluorescence that occurs distal from sample 29 does not fall within the through-focus-curve of objective 27. This auto-fluorescence does not reach detector 39 by following the path of retro-beam 31. Rather, auto-fluorescence that emanates distally from sample 29 appears to detector 39 to radiate spherically from a point source, referred to as spherical auto-fluorescence (SAF).

Typically, the net flux of auto-fluorescent photons that reach detector 39 resulting from TFA exceeds the number of auto-fluorescent photons reaching detector 39 resulting from SAF. Upon analyzing the source of TFA, it was discovered that the same was caused by sample components, e.g., the slide and sample, as well as objective lens 27. With respect to objective lens 27, the source of the TFA was attributed to the material from which the optical elements were made, as well as the adhesive which was used to hold the same together.

To determine the amount of auto-fluorescence attributed to adhesives, a series of tests were conducted on glass lens elements typically employed to make complex lens systems, such as objective lens 27. The adhesives tested were manufactured by Summers Optical, a Division of EMS Acquisition which is located in Fort Washington, Pa. under tradenames J-91 and UV-74. The test was conducted by having two different wavelengths $\lambda$ of light impinging upon the lens. For each wavelength $\lambda$, the number of photons attributable to TFA was measured using a photomultiplier tube. For $\lambda=532$ nm, the results were as follows:

| Adhesive applied | Average number of photons sensed |
|---|---|
| J-91 | 9200 |
| UV-74 | 47069 |
| none | 3982 |
| For $\lambda$ = 633 nm, the results were as follows: | |
| J-91 | 1400 |
| UV-74 | 1853 |
| none | 1330 |

Tables 3 and 4 show that an appreciable amount of TFA is attributable to the adhesives disposed on portions of the lens elements of the objective 27 that lie in an optical path. Further, it is shown that the amount of TFA produced by a given adhesive is wavelength dependent. Therefore, it was discovered that by removing adhesive from these portions of the lens elements that comprise objective lens 27, TFA associated therewith may be greatly reduced and rendered wavelength independent. Thus, an objective lens may be provided that affords improved signal-to-noise ratio and is suitable for use with a plurality of wavelengths of light.

Figure 9:
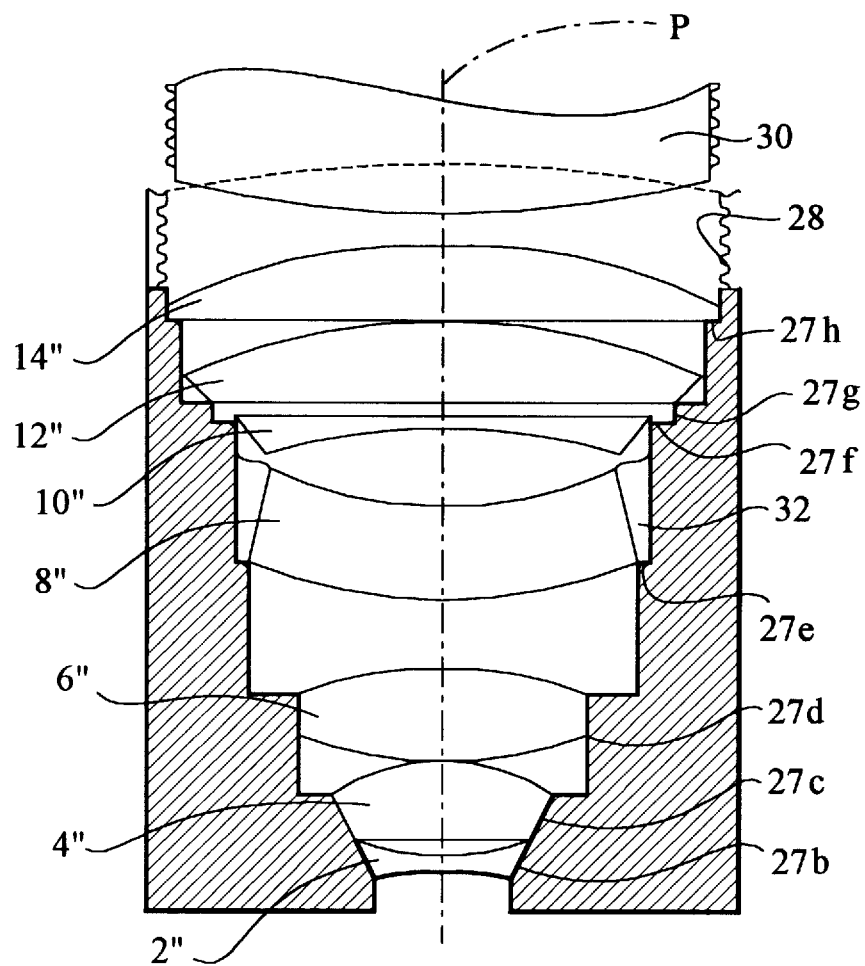
FIG. 9 is a plan view of the housing in which the optical elements shown in FIG. 7 are placed.

Referring to FIG. 9, shown is one embodiment of a lens housing 27a, which is required to fix the spatial position of the lens elements along the optical path "P". As can be seen, lens housing 27a includes a plurality of step portions which form annular shoulders, each of which supports a lens element. Specifically, lens elements 2", 4", 6", 8", 10", 12" and 14" rest against annular shoulders 27b, 27c, 27d, 27e, 27f, 27g, and 27h, respectively. To fix the position of each of the lens elements, one end of housing 27a includes a plurality of threads 28. A hollow cylinder 30 is adapted to engage threads 28 and press against lens element 14". In this fashion, the lens elements of objective lens 27 are held in place without necessitating the use of adhesives in the optical path, defining an air-space objective lens. In airspaced objective lenses, each of the plurality of lens elements, 27b, 27c, 27d, 27e, 27f, 27g and 27h, is spaced apart from an adjacent lens element. This avoids having adhesives disposed in optical path "P". When mounted in the system, lens element 27b is positioned proximate to sample 29.

Figure 10:
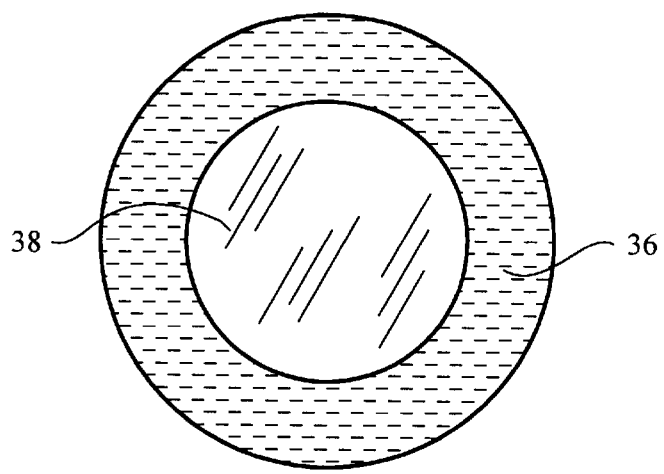
FIG. 10 is a simplified plan view of a lens element that may be employed in the objective lens of the present invention.

Alternatively, lens elements 27b, 27c, 27d, 27e, 27f, 27g, and 27h may be adhered to housing 27a, without disposing any adhesive in optical path "P". To that end, adhesive could be placed at the periphery of each of the lens elements so that the side edge of the lens elements are adhered to the side of housing 27a. This is shown, for example, with adhesive 32 disposed between housing 27a and lens element 8". Should it be necessary to apply adhesive between two lens elements to fix the same together, the adhesive may be disposed as an annular ring 36, shown in FIG. 10. This would leave the central portion of lens 38 without adhesive so the same could be placed in optical path "P". Employing an annular ring 36 of adhesive allows taking advantage of paraxial image while avoiding TFA.

Figure 11:
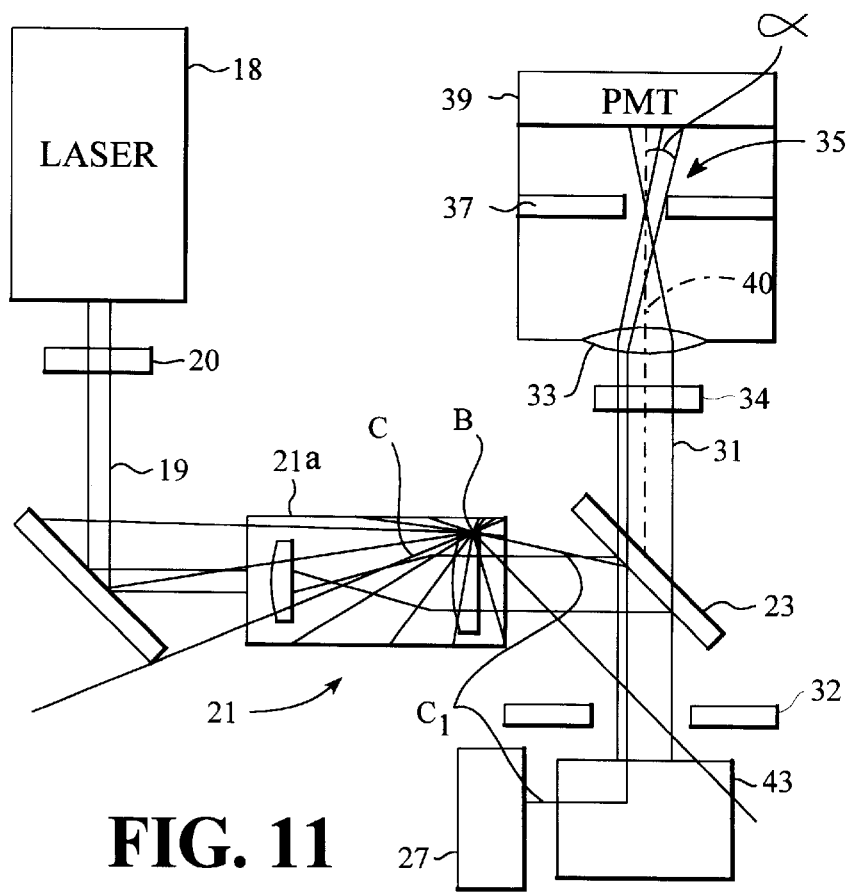
FIG. 11 is a detailed view of a portion of the optical components shown in FIG. 2 and including a line filter to block auto-fluorescence.

Referring to FIG. 11, to further reduce the autofluorescence in the system due to spherical autofluorescence (SAF), filters were placed at various points in the optical path. Specifically, as discussed above, it was discovered that SAF appears, to detector 39, to radiate spherically from a point source. Because field-stop 37 is positioned proximate to photodetector 39 in the retro-path, the SAF that may impinge upon photodetector 39 depends upon two variables. The aforementioned variables are the distance "d" between the point source of SAF and the angle a between the point source and the retro-path 40, with retro-path 40 being defined as the path light travels from beam splitter 23 and photodetector 39.

For example, it was discovered that SAF emanated from optical elements of beam expander 21. Were SAF to be produced at point B, the same would radiate outwardly shown as rays C. As can be seen, the angle $\alpha$ of ray $C_1$ is sufficient to allow the same to propagate through the aperture 35 in field stop 37. This results in ray $C_1$ reflecting from various optical elements in the optical path so it appears collimated to the photodetector 39, i.e., travels parallel to retro-path 40. As shown, ray $C_1$ has reflected from objective 27 to impinge upon focusing lens 33, where it is directed onto photodetector 39. A substantial number of the rays C are blocked by the encasement 21a which houses beam expander 21. To block ray $C_1$ and any other ray that may impinge upon photodetector 39, a line filter 22 may be placed between beam expander 21 and beam splitter 23 that allows only the passage of beam 19 therethrough. The line filter 22 must have sufficient dimensions to block light radiating from point source B over a solid angle so as to prevent SAF from passing through aperture 35. In this fashion, SAF from the optical components of beam expander 21 would not impinge upon photodetector 39.

It was discovered that condenser lens 33 also produces SAF. This resulted from reflection of beam 19 from sample 29 and the inefficiency of beam splitter 23. Although beam splitter 23 functions to separate beam 19 from beam 31, analysis showed that a portion of beam 19 that reflects from sample 29 passes through beam splitter 23. As a result of that portion of beam 19 impinging upon condenser lens 33, SAF is produced. Although the SAF produced at condenser lens 33 is de minimus compared to that produced at point B, the net flux that travels through aperture 25 is higher. This results from condenser lens 33 laying in retro-path 40, which increases the probability that photons associated with SAF will pass through aperture 25. Specifically, a substantial amount of rays of SAF produced by condenser lens 33 travel parallel to retro-path 40. This coupled with the relatively short distance between condenser lens 33 and photodetector 39 results in a greater amount of SAF reaching the sample when compared to the SAF produced at beam expander 21. To avoid SAF being produced by the condenser lens 33, band pass filter 34 is disposed between the beam splitter 23 and the condenser lens 33 to reject excitation wavelengths while being transmissive to wavelengths associated with beam 31.

Figure 12:
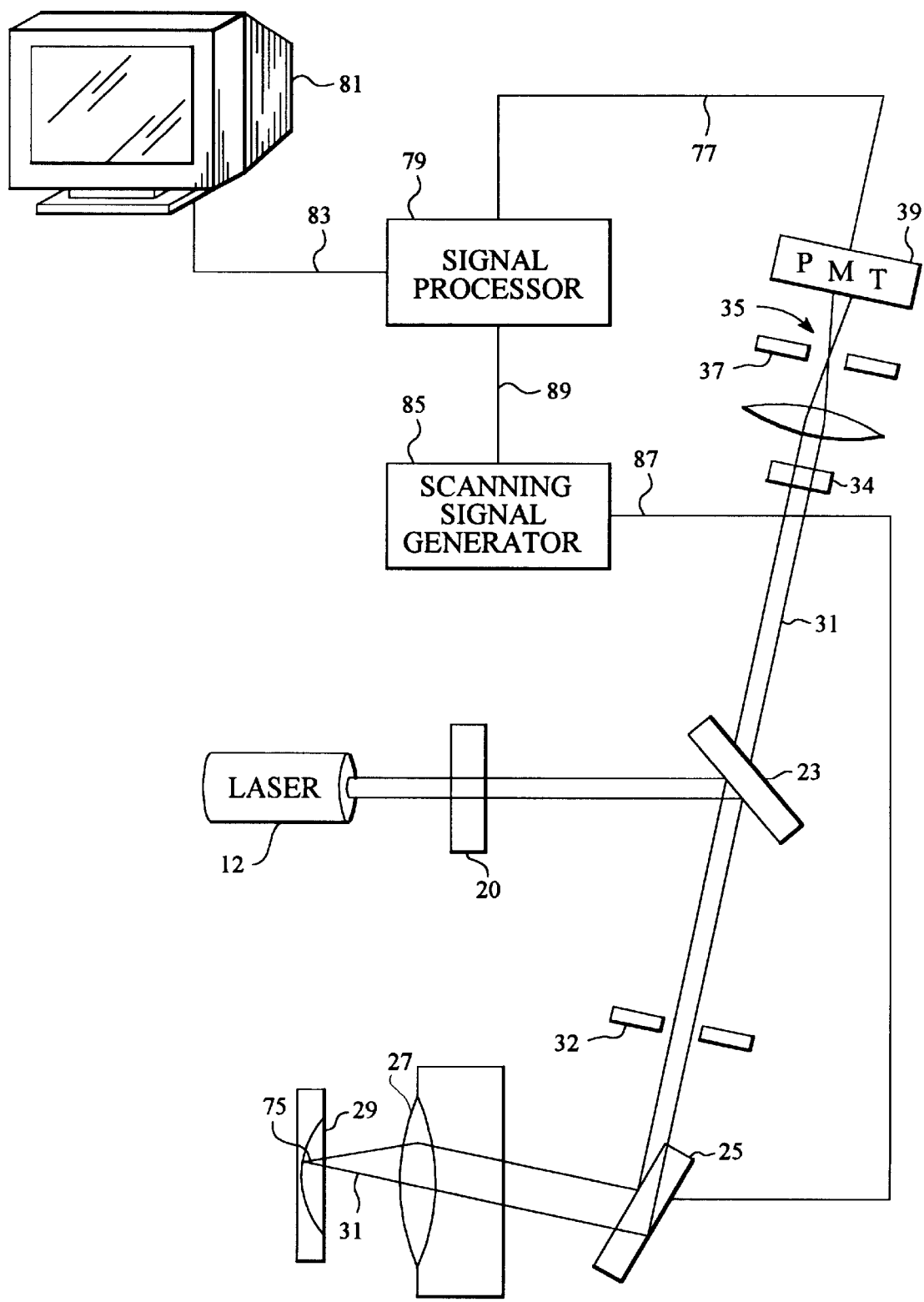
FIG. 12 is a simplified side view of the optical components shown on FIG. 2, including a video display system to reproduce an image of the sample in accordance with the present invention.

Referring to FIG. 12, the operation of the system is discussed. Preferably, the system is to take advantage of detection using the conjugate focal (confocal) technique. In this manner, retro-beam 31 is shown emanating from a point 75 which corresponds to a point source of light illuminated by an incident beam which was focused to a diffraction limited spot on sample 29. Retro-beam 31 is imaged on detector 39, after passing through aperture 35. Aperture 35, in spatial filter 37, isolates the detection of the system to that substantially coincident with the illuminating spot so that aperture 35 and point 75 are optically conjugated with each other. Although any light detector may be used, it is preferred to use a photomultiplier tube. The signal from the photomultiplier tube passes through electrical connections 77 to a signal processor 79 of a video display system including a video display screen 81. The signal from the photomultiplier tube 39 modulates the intensity of the image signal transmitted from the processor 79 through the output line 83 to the display screen 81. A scanning signal generator 85, under control of the signal processor 79 via line 89, supplies electrical signals to the scanning apparatus 25 through electrical connections 87. The scanning apparatus 25 moves in response to the generator 85's signals. The signal from photomultiplier tube 39 is digitized and stored in memory and can be simultaneously scanned onto a display.

Although fluorescent confocal imaging is the preferred embodiment, the system may be used in a non-confocal manner. In this fashion, field stop 37 and aperture 35 may filter light in a either non-confocal or semi-confocal manner. In either manner, spatial filter 37 and aperture 35 improve the signal to noise ratio. Pupil stop 32 is configured to control the numerical aperture of the objective lens with respect to retro-beam 31. Without pupil stop 32, the numerical aperture at a given scan angle would be established by vignetting of objective lens 27. In effect, pupil stop 32 increases retro beam 31's intensity uniformity across objective lens 27's field of view and defines both the diameter of retro-beam 31 impinging upon focusing lens 33, and, therefore, the numerical aperture of the system. Although pupil stop 32 is shown positioned between scanning device 25 and beam splitter 23, pupil stop 32 may be positioned anywhere in the retro path between scanning device 25 and focusing lens 33.

An obvious extension of the system is in the area of reflection imaging. That is, the reflected laser beam could be collected at the detector instead of the fluorescent beam. Both the reflected beam and the fluorescent beam could be read at a different detector if a second dichroic beam splitter was positioned after the primary dichroic beam splitter. Or in a like manner, multiple fluorescent labels could be detected by using multiple secondary beam splitters and detectors.

Figure 13:
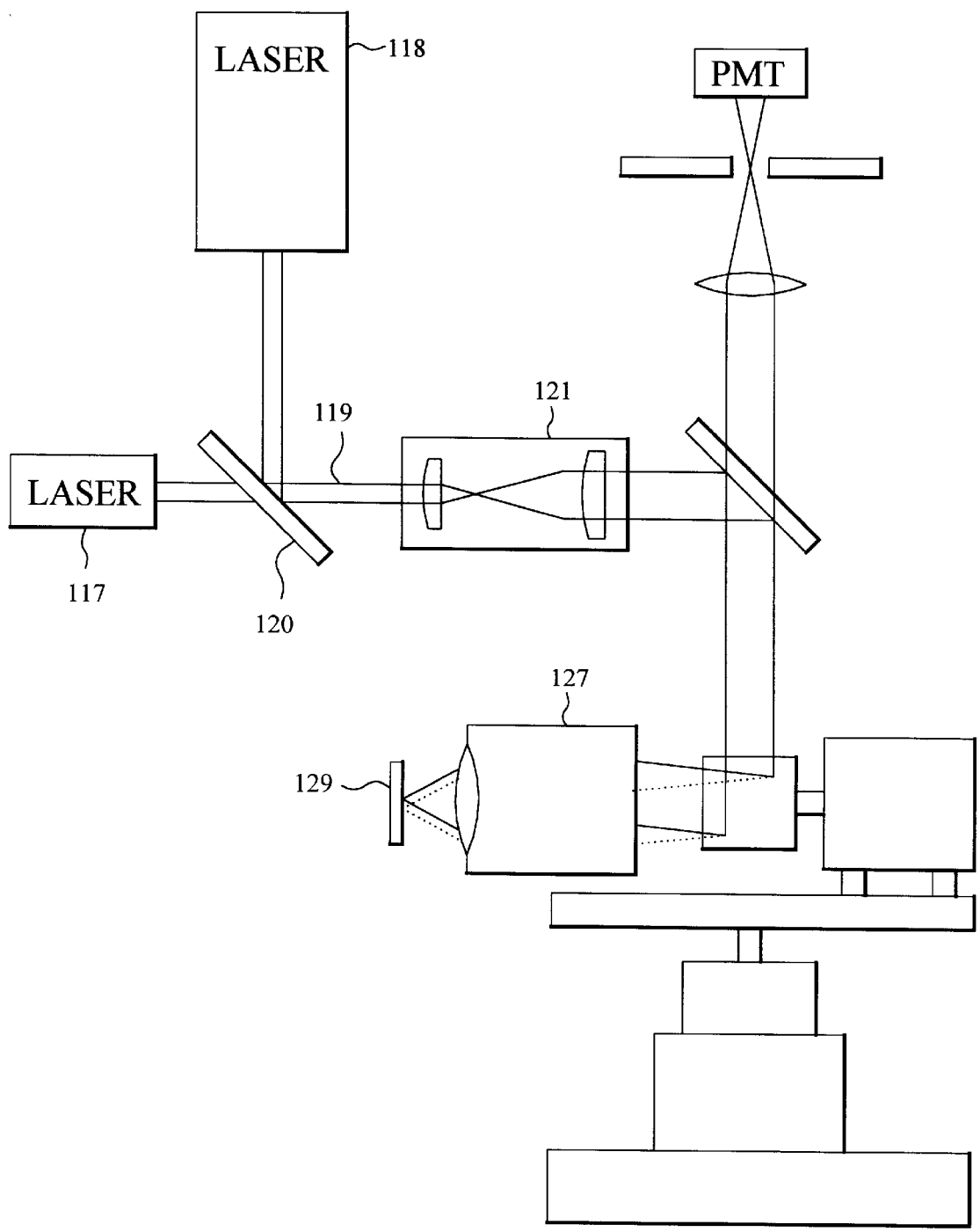
FIG. 13 is a side view of the invention shown in FIG. 2 in accord with an alternate embodiment.

Referring to FIG. 13, a second embodiment of the present invention is shown in which a further benefit of having all axial chromatic aberrations corrected in the retro-path is described. The second embodiment of the system includes all of the features of the systems described above with respect to FIG. 1, except two or more light sources 117 and 118 are provided, each of which emits a wavelength different from the remaining light source, forming an incident beam 119 comprising multi-chromatic light. The light sources may be utilized simultaneously, or each could be scanned individually by turning-off, or shuttering, the undesired light source. A beam expander 121 is optically coupled to at least one of the light sources 117 and 118 to control the collimated beam diameter and to correct for any axial chromatic aberrations in the system along the incident beam 119 path. In this fashion, substantially all light comprising incident beam 119 will impinge upon the same focal plane of sample 129. This is particularly useful for providing a highly efficient confocal imaging system.

Each light source 117 and 118 may be uniquely associated with a beam expander. It is preferred, however, that all light sources are in optical communication with a common beam expander, as shown, in order to reduce both the size and cost of the system. To that end, a dichroic filter 120 is disposed between light sources 117 and 118 and beam expander 121. Dichroic filter 120 allows light from source 117 to pass through while reflecting light from source 118 so that the light from both form incident beam 119 before entering beam expander 121. Beam expander 121 has optical properties that introduce axial chromatic aberrations to cancel axial chromatic aberrations introduced by optical elements, e.g., objective lens 127 in the system following beam expander 121 to ensure all wavelengths of light comprising beam 119 impinge upon the same focal plane of sample 129.

Figure 14:
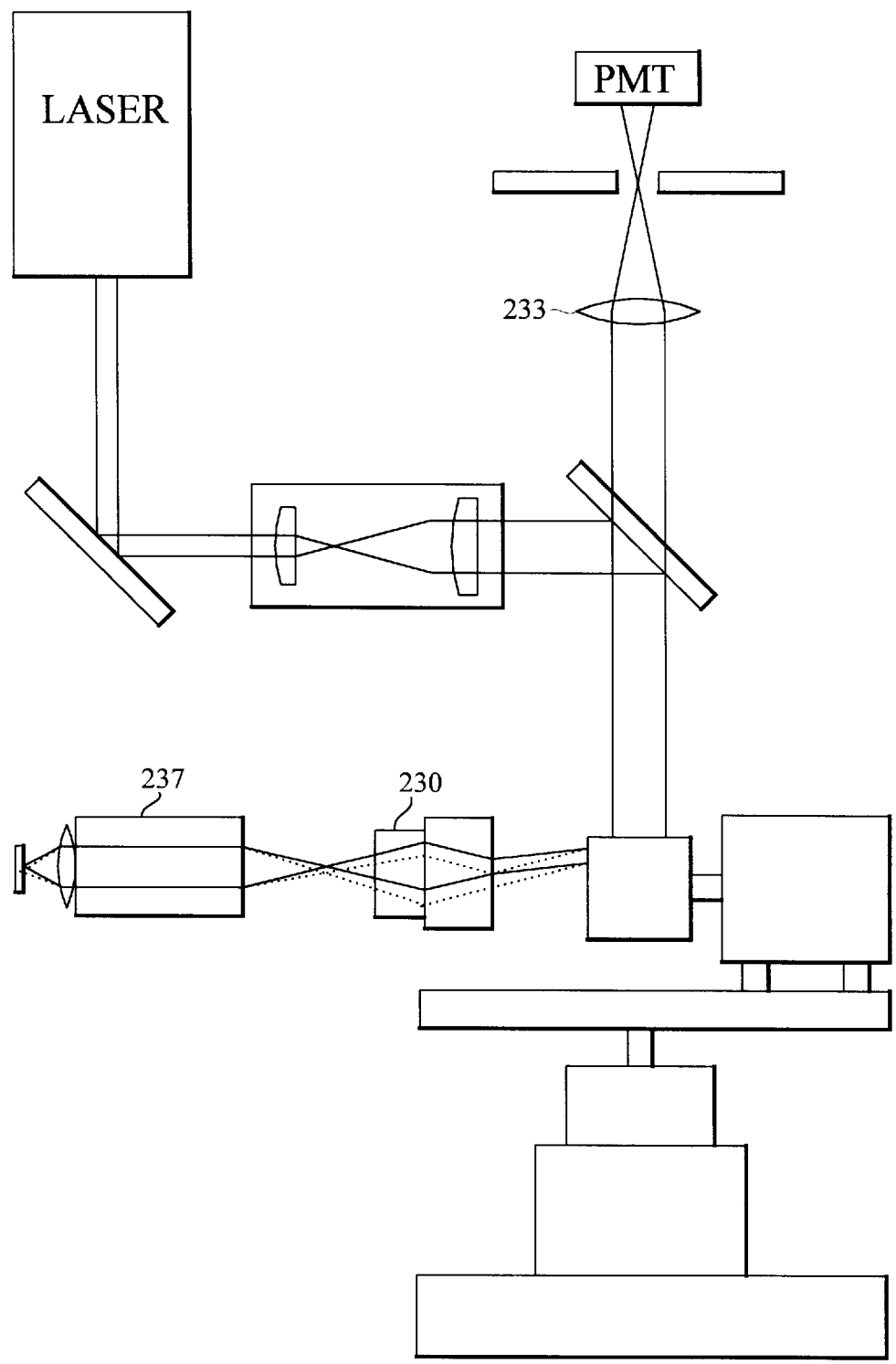
FIG. 14 is a side view of an alternate embodiment of the present invention.

Referring to FIG. 14, shown is another objective lens system that may be employed by having all axial chromatic aberrations corrected in the retro-path. The collection lens 233 may be used in a microscope style system. In such a system, objective lens 227 is optically coupled to reflecting element 243 via an eye piece 230. The remaining elements of the system are identical to those shown in FIG. 2.

We claim:

1. A fluorescence microscopy system for stimulating a sample to fluoresce, said system comprising:

a photodetector;

a source for emitting an excitation beam of light along an optical path, said excitation beam having optical properties to cause said sample to fluoresce;

an air-spaced objective disposed in said optical path to receive said excitation beam therethrough to illuminate a region of said sample and collect fluorescent light emitted from said region, forming a retro-beam, said objective including a plurality of lens elements, with each of said plurality of lens elements being spaced-apart from an adjacent lens element of said air-spaced objective, thereby avoiding the presence of adhesives in the portion of the optical path so as to reduce auto-fluorescence produced by said air-spaced objective;

means, positioned in said optical path between said source and said objective, for separating said excitation beam from said retro-beam, wherein said objective directs said retro-beam onto said separating means, with said separating means directing said retro-beam toward said photodetector, said photodetector producing signals representing light impinging thereon; and beam shaping optics disposed in said optical path, said beam shaping optics having optical properties to produce auto-fluorescence in response to said excitation beam impinging thereon, and filtering means, disposed in said optical path, for reducing the auto-fluorescence sensed by said detector.

2. A fluorescence microscopy system for stimulating a sample to fluoresce, said system comprising:

a photodetector;

a source for emitting an excitation beam of light along an optical path, said excitation beam having optical properties to cause said sample to fluoresce;

an air-spaced objective disposed in said optical path to receive said excitation beam therethrough to illuminate a region of said sample and collect fluorescent light emitted from said region, forming a retro-beam, said objective including a plurality of lens elements, with each of said plurality of lens elements being spaced-apart from an adjacent lens element of said air-spaced objective, thereby avoiding the presence of adhesives in the portion of the optical path so as to reduce auto-fluorescence produced by said air-spaced objective;

means, positioned in said optical path between said source and said objective, for separating said excitation beam from said retro-beam, wherein said objective directs said retro-beam onto said separating means, with said separating means directing said retro-beam toward said photodetector, said photodetector producing signals representing light impinging thereon; and beam shaping optics disposed in said optical path, said beam shaping optics having optical properties to produce auto-fluorescence that radiates spherically in response to said excitation beam impinging thereon and a filtering means, disposed in said optical path, for attenuating auto-fluorescence propagating over a solid angle of sufficient size to prevent said auto-fluorescence from impinging upon said photodetector.

3. A fluorescence microscopy system for stimulating a sample to fluoresce, said system comprising:

a photodetector;

a source for emitting an excitation beam of light along an optical path, said excitation beam having optical properties to cause said sample to fluoresce;

an air-spaced objective disposed in said optical path to receive said excitation beam therethrough to illuminate a region of said sample and collect fluorescent light emitted from said region, forming a retro-beam, said objective including a plurality of lens elements, with each of said plurality of lens elements being spaced-apart from an adjacent lens element of said air-spaced objective, thereby avoiding the presence of adhesives in the portion of the optical path so as to reduce auto-fluorescence produced by said air-spaced objective;

means, positioned in said optical path between said source and said objective, for separating said excitation beam from said retro-beam, wherein said objective directs said retro-beam onto said separating means, with said separating means directing said retro-beam toward said photodetector, said photodetector producing signals representing light impinging thereon; and beam shaping optics disposed in said optical path, said beam shaping optics having optical properties to produce auto-fluorescence in response to said excitation beam impinging thereon and a filtering means, disposed to in said optical path, for attenuating light associated with said excitation beam, thereby preventing the same from impinging upon said beam shaping optics.

4. A fluorescence microscopy system for stimulating a sample to fluoresce, said system comprising:

a photodetector;

a source for emitting an excitation beam of light alone an optical path, said excitation beam having optical properties to cause said sample to fluoresce;

an air-spaced objective disposed in said optical path to receive said excitation beam therethrough to illuminate a region of said sample and collect fluorescent light emitted from said region, forming a retro-beam, said objective including a plurality of lens elements, with each of said plurality of lens elements being spaced-apart from an adjacent lens element of said air-spaced objective, thereby avoiding the presence of adhesives in the portion of the optical path so as to reduce auto-fluorescence produced by said air-spaced objective;

means, positioned in said optical path between said source and said objective, for separating said excitation beam from said retro-beam, wherein said objective directs said retro-beam onto said separating means, with said separating means directing said retro-beam toward said photodetector, said photodetector producing signals representing light impinging thereon; and wherein said objective has optical properties to provide a substantially uniform detection sensitivity across said field of view by introducing, into said system, a specified amount of axial chromatic aberrations while reducing lateral chromatic aberrations and a focusing lens means, disposed in the path of said retro-beam, for directing said retro-beam onto said photodetector and further including a focusing lens means, disposed between said objective and said photodetector, for reducing axial chromatic aberrations introduced by said objective.

5. A fluorescence microscopy system for stimulating a sample to fluoresce, said system comprising:

a photodetector;

a source for emitting an excitation beam of light along an optical path, said excitation beam having optical properties to cause said sample to fluoresce;

an air-spaced objective disposed in said optical path to receive said excitation beam therethrough to illuminate a region of said sample and collect fluorescent light emitted from said region, forming a retro-beam, said objective including a plurality of lens elements, with each of said plurality of lens elements being spaced-apart from an adjacent lens element of said air-spaced objective, thereby avoiding the presence of adhesives in the portion of the optical path so as to reduce auto-fluorescence produced by said air-spaced objective;

means, positioned in said optical path between said source and said objective, for separating said excitation beam from said retro-beam, wherein said objective directs said retro-beam onto said separating means, with said separating means directing said retro-beam toward said photodetector, said photodetector producing signals representing light impinging thereon; and wherein said separating means includes a mirror having a diameter greater than the diameter of said incident beam and smaller than the diameter of said retro-beam, with the diameter of the retro-beam being substantially larger than the diameter of the incident beam.

6. A fluorescence microscopy system for stimulating a sample to fluoresce, said system comprising:

a photodetector;

a source for emitting an excitation beam of light along an optical path, said excitation beam having optical properties to cause said sample to fluoresce;

an objective disposed in said optical path to receive said excitation beam therethrough to illuminate a region of said sample and collect fluorescent light emitted from said region, forming a retro-beam;

a spatial filter, positioned proximate to said photodetector, having a substantially transmissive aperture, restricting light scattered rearwardly to increase signal response;

a focusing lens means, disposed in the path of said retro-beam, for directing said retro-beam onto said aperture, and onto said photodetector, with said photodetector producing signals representing light impinging thereon, said focusing lens means having optical properties to produce auto-fluorescence in response to said excitation beam passing therethrough; and first filtering means, disposed in said optical path between said focusing lens means and said separating means, for reducing the auto-fluorescence sensed by said detector.

7. The systems as recited in claim 6 wherein said objective includes a plurality of lens elements, a subset of which has an adhesive attached thereto to fix a spatial position, along said optical path, between said subset and the remaining lens elements of said plurality of lens elements, with all said adhesive present in said objective lens disposed upon said subset outside of said optical path, with said excitation beam passing through said objective lens without impinging upon said adhesive, thereby reducing auto-fluorescence.

8. The system as recited in claim 6 further including means, positioned in said optical path between said beam source and said objective, for separating said incident beam from said retro-beam, and a beam expander disposed in said optical path between said source and said separating means, said beam expander having optical properties to produce auto-fluorescence that radiates spherically in response to said excitation beam impinging thereon, with a second filtering means, disposed between said beam expander and said source, for attenuating auto-fluorescence propagating over a solid angle of sufficient size to prevent the same from passing through said transmissive aperture.

9. The system as recited in claim 6 further wherein objective has optical properties to provide a substantially uniform detection sensitivity across said field of view by introducing, into said system, a specified amount of axial chromatic aberrations while reducing lateral chromatic aberrations and a focusing lens means, disposed in the path of said retro-beam, for directing said retro-beam onto said photodetector said focusing lens means having optical properties to compensate for axial chromatic aberrations introduced by said objective.

10. The system as recited in claim 6 further including means, positioned in said optical path between said beam source and said objective, for separating said incident beam from said retro-beam, wherein said separating means includes a mirror having a diameter greater than the diameter of said incident beam and smaller than the diameter of said retro-beam, with the diameter of the retro-beam being substantially larger than the diameter of the incident beam.

11. The system as recited in claim 6 further including means, positioned in said optical path between said beam source and said objective, for separating said incident beam from said retro-beam, and a pinhole disposed in said optical path and a collimating lens positioned to collimate light passing through said pinhole, with said pinhole disposed between said beam source and said separating means, and said collimating lens disposed between said separating means and said pinhole, wherein said beam source is a non-coherent source of light optically focused on said pinhole.

12. A fluorescence microscopy system for stimulating a sample to fluoresce, said system comprising:

a photodetector;

a source for emitting an excitation beam of light along an optical path, said excitation beam having optical properties to cause said sample to fluoresce;

an air-spaced objective disposed in said optical path to receive said excitation beam therethrough to illuminate a region of said sample and collect fluorescent light emitted from said region, forming a retro-beam; said objective including a plurality of lens elements, with each of said plurality of lens elements being spaced-apart from an adjacent lens element of said objective;

a spatial filter, positioned proximate to said photodetector, having a substantially transmissive aperture, restricting light scattered rearwardly to increase signal response;

a focusing lens means, disposed in the path of said retro-beam, for directing said retro-beam onto said aperture, and onto said photodetector, with said photodetector producing signals representing light impinging thereon, said focusing lens means having optical properties to produce auto-fluorescence in response to said excitation beam passing therethrough;

means, positioned in said optical path between said beam source and said objective, for separating said incident beam from said retro-beam, said separating means directing said retro-beam toward said photodetector, with said photodetector producing signals representing light impinging thereon; and first filtering means, disposed in said optical path between said focusing lens means and said separating means, for reducing the auto-fluorescence sensed by said detector.

13. The system as recited in claim 12 further including means, positioned in said optical path between said beam source and said objective, for separating said incident beam from said retro-beam, and a beam expander disposed in said optical path between said source and said separating means, said beam expander having optical properties to produce auto-fluorescence that radiates spherically in response to said excitation beam impinging thereon, with a second filtering means, disposed between said beam expander and said source, for attenuating auto-fluorescence propagating over a solid angle of sufficient size to prevent the same from passing through said transmissive aperture.

14. The system as recited in claim 12 further wherein objective has optical properties to provide a substantially uniform detection sensitivity across said field of view by introducing, into said system, a specified amount of axial chromatic aberrations while reducing lateral chromatic aberrations and a focusing lens means, disposed in the path of said retro-beam, for directing said retro-beam onto said photodetector said focusing lens means having optical properties to compensate for axial chromatic aberrations introduced by said objective.

15. The system as recited in claim 12 further including means, positioned in said optical path between said beam source and said objective, for separating said incident beam from said retro-beam, wherein said separating means includes a mirror having a diameter greater than the diameter of said incident beam and smaller than the diameter of said retro-beam, with the diameter of the retro-beam being substantially larger than the diameter of the incident beam.

16. The system as recited in claim 12 further including means, positioned in said-optical path between said beam source and said objective, for separating said incident beam from said retro-beam, and a pinhole disposed in said optical path and a collimating lens positioned to collimate light passing through said pinhole, with said pinhole disposed between said beam source and said separating means, and said collimating lens disposed between said separating means and said pinhole, wherein said beam source is a non-coherent source of light optically focused on said pinhole.

* * * * *